United States Patent [19]
Rüsse et al.

[11] Patent Number: 4,696,914
[45] Date of Patent: Sep. 29, 1987

[54] MATERIAL FOR IMPROVING THE FERTILITY OF MAMMALS AND PROCESS FOR ITS PRODUCTION

[75] Inventors: Meinhard W. Rüsse, Schnaitsee; Rudolf Bolze, Hanau; Friedhelm Koch, GroBkrotzenburg, all of Fed. Rep. of Germany

[73] Assignee: Degussa Aktiengesellschaft, Frankfurt am Main, Fed. Rep. of Germany

[21] Appl. No.: 888,570

[22] Filed: Jul. 23, 1986

[30] Foreign Application Priority Data

Jul. 31, 1985 [DE] Fed. Rep. of Germany ....... 3527356

[51] Int. Cl.$^4$ .............................................. A61K 37/02
[52] U.S. Cl. ..................................... 514/19; 514/567; 514/538

[58] Field of Search ................ 562/445; 514/561, 899, 514/567, 19, 21, 538; 424/14

[56] References Cited

U.S. PATENT DOCUMENTS 3,362,879  1/1918  Udenfriend et al. ................ 562/445
3,941,763  3/1976  Sarantakis ............................. 514/15
4,218,474  8/1980  Barnish et al. ...................... 514/620

Primary Examiner—J. R. Brown
Assistant Examiner—F. T. Moezie
Attorney, Agent, or Firm—Cushman, Darby & Cushman

[57] ABSTRACT

The fertility of female mammals can be improved by dispensing once or within a short time repeatedly a high dosage of tyrosine. The dispensation can be carried out at will intravenously or orally.

18 Claims, No Drawings

MATERIAL FOR IMPROVING THE FERTILITY OF MAMMALS AND PROCESS FOR ITS PRODUCTION

BACKGROUND OF THE INVENTION

The invention is directed to a material or agent for improving the fertility of mammals.

The agent of the invention is especially suited for improvement the fertility of sexually mature female mammals. By improvement of fertility there is meant that, e.g., in female animals the cycle is stimulated and normalized. The use of the agent is particularly suitable with domestic animals such as cattle, sheep, horses, and sows, as well as with dogs and cats.

Tyrosine belongs to the aminoacids occurring in nature and is a component of proteins. It can be formed from the essential aminoacid phenylalanine and, therefore, is only classified as semi-essential. Tyrosine represents the most important metabolite of phenylalanine. The synthesis occurs first and foremost in the liver and to a limited extent in the brain.

Besides their function as building blocks in the protein metabolism phenylalanine and tyrosine also fulfill special tasks as forerunners of hormones. Thus, there are derived from tyrosine and phenylalanine, for example, dopamine, noradrenaline, adrenaline and tyroxine.

It was thought that the synthesis of tyrosine from phenylalanine frequently is not sufficient to cover the tyrosine requirement of the organism at any point in time.

It is known that phenylalanine and tyrosine, more preferably, however, specific derivatives of these aminoacids can be used to control blood pressure and to stimulate the appetite. There is based on this the observation that there can be stimulated the biosynthesis of catecholamines, above all else the synthesis of noradrenaline, by increased addition of tyrosine. This neurotransmitter leads to a normalizing regulation of metabolism and physiological stimulating conditions.

SUMMARY OF THE INVENTION

The present invention is based on the unexpected discovery that by supplying high amounts of tyrosine once or repeatedly within two days, preferably 1-4 times, the occurrence of fertility in domestic animals can be controlled in such fashion that this high feeding of tyrosine can lead to a stimulation of the cycle and normalization.

The agent of the invention is used in such manner that there is dispensed to the animal once or within a short period of time repeated by doses of tyrosine in an amount between 30 and 200 mg per kg body weight, preferably 80-120 mg per kg, in which daily doses of 1-50 grams of tyrosine are dispensed depending on the animal.

The tyrosine can be dispensed intravenously, for example, in the form of a physiologically compatable solution, preferably in the form of a solution in sterile physiological salt solution. There are suited for this purpose short chain peptides, especially N-glycyl-L-tyrosine, N-acetyl-L-tyrosine and alkyl esters of tyrosine having 1-5 carbon atoms, e.g., the methyl, ethyl, propyl, isopropyl, butyl or amyl esters, or the hydrochloride of these compounds, as well as salts of tyrosine, e.g., the sodium and potassium compounds.

Alternatively thereto the tyrosine can also be dispensed as such in the form of its potassium, sodium, magnesium or calcium salt or in the form of a physiologically compatible derivative from which tyrosine is set free in the digestive tract. Suitable tyrosine derivatives for example are the N-hydroxymethyl derivative, the N-acetyl and N-glycyl derivative or the N-acyl derivatives with straight or branch chain, saturated acyl groups having 8-22 carbon atoms, e.g., the octanoyl group, decanoyl group, lauroyl group, palmitoyl group, stearoyl group, oleoyl group, eicosanoyl group.

With ruminants orally dispensed aminoacids for the most part are broken microbially in the rumen. Therefore, if tyrosine is to be available in a larger extent in the metabolism it must be protected against this breakdown through microorganisms in the rumen. Various methods are suited for the protection of this aminoacid before bacterial breakdown. For one the tyrosine can be converted chemically to derivatives. Derivatives which pass through the rumen substantially without breakdown for example are the already mentioned N-hydroxymethyl and N-acyl derivatives. However, on the other hand, tyrosine can also be dispensed as such in the form of coated particles. As coating agent for the tyrosine to be protected there can be used suitable polymer. However, materials such as long chain fatty acids with for example 14 to 22 carbon atoms and their glycerides are better. Thus, there can be used, for example myristic acid, palmitic acid, stearic acid, oleic acid, behenic acid, glyceryl tristearate, glyceryl trioleate, glyceryl tripalmitate. An especially advantageous coating agent is a mixture of the free fatty acids and the sodium, potassium or calcium salts of aliphatic monocarboxylic acids present having 14–22 carbon atoms. The fatty acids can be saturated or unsaturated, branched or non-branched, preferably, the non-branched fatty acids occurring in natural fats such as myristic acid, palmitic acid, stearic acid, trachinic acid or behenic acid or mixtures of such acids. The mixture preferably can consist of 50 to 90 weight percent of acid and 10 to 50 weight percent salt. There can also be used hydrogenated fats having melting points of 40°-60° C. Advantageously their structures are fixed by suitable procedures as micro particles, so that they are more readily accessible to resorption. In oral dispensation of tyrosine, tyrosine derivatives or coated particles it can be suitable for facilitation and to guarantee a complete absorption of the intended amount of tyrosine to encapsulate the preparation to be dispensed in gelatin capsules. The daily dosage thereby, e.g., can be divided into 2 or 4 soft gelatin capsules which are dispensed with a pill dispenser either simultaneously or in an interval of several hours successively.

With dogs it was observed that after dispensing of a single dose of tyrosine of 100 mg per kg bodyweight the covering of this type of treated bitch proceeds especially successfully. The tyrosine thereby exerts a clear influence on the cycle which could not be expected from the nutritive or the hormonal functions of this aminoacid or its derivatives.

With mother sows the rutting after weaning can be favorably influenced by the oral dispensation of tyrosine. Insofar as no rutting occurs after weaning this can also be released after a long time by a single dispensation of tyrosine. It is surprising that with sows treated with tyrosine there can be recognized an about 20% increased number of piglets per litter.

In further experiments the same effect could also be produced by intravenous infusion of a physiologically compatible readily soluble tyrosine derivative. Thereby there was used, e.g., a solution of 2% N-glycyl-1-tyrosine in physiological salt solution. For infusion solutions there are preferably used solutions with 0.2-5% of tyrosine derivative.

Cows which were given tyrosine dispensed in a form protected by fatty acids and alkali metal salts of fatty acids were rutting after 3 days and could be inseminated with a higher rate of conception. For addition with milk cows a mixture of 20 to 40 weight percent of the coated mixture and 60 to 80 weight percent tyrosine has been found to be especially advantageous. However, there can also be used mixtures with lower tyrosine contents. It is understood there can also be used together with the tyrosine other nutrients or active materials, for example, other aminoacids or vitamins, protected and dispensed in this form to the ruminants.

There can be used for dispensation, for example, to sexually mature female mammals, e.g., milk cows, horses, sheep, sows, dogs and cats a dosage unit of 1 to 10,000 mg, preferably 5 to 4000 mg of tyrosine or a tyrosine derivative corresponding to an equivalent amount of a tyrosine.

There can be produced materials according to the invention which contain 50-90 weight percent tyrosine present as such or in the form of a derivative by mixing or homogenizing with customary carriers, and/or diluents, respectively adjuvants at a temperature between 20° and 60° C. and using the thus obtained mixture to produce granulates which contain 1-200 mg tyrosine, pills, pellets or tablets which contain 10 to 500 mg tyrosine or briquettes which contain 200-10,000 mg of tyrosine. The mixture can also be fitted into gelatin capsules so that there are 200-10,000 mg of tyrosine in the dosage unit.

The agent can be prepared by mixing 50-90 weight percent tyrosine whereby the tyrosine also can be present in the form of a derivative, optionally with at least one fodder adjuvant such as e.g., wheat bran, starch, microcrystalline cellulose, calcium hydrogen phosphate or lactose or there can be added a granulating aid such as, e.g., methyl cellulose or an aqueous gelatin solution or granulated starch solution or the mixture can be pressed into tablets or pellets and/or filled into capsule.

The product of the invention can also be prepared by suspending and homogenizing. 50-90 weight percent tyrosine or tyrosine in the form of a derivative, optionally after addition of an emulsifier or fatty acid ester, e.g, lecithin or monoester of 1,2-propanediol with food grade fatty acids (e.g., stearic acid, myristic acid) at a temperature between 40°-60° C. in melted hard fat or in a mixture of aliphatic monocarboxylic acids having 14-22 carbon atoms, i.e., fatty acids, and their sodium, potassium, calcium or magnesium salts and subsequently pouring the mixture into hollow cells or pressing to pellets under suitable conditions on a pellet press or pressing into briquettes.

The composition can comprise, consist essentially of, or consist of the stated materials and the process can comprise, consist essentially of, or consist of the recited steps with such materials.

Unless otherwise indicated, all parts and percentages are by weight.

The invention will be explained in further detail in the following examples.

DETAILED DESCRIPTION

EXAMPLE 1

There were dispensed to six German spotted cows over a time period of 4 days L-tyrosine at a dosage of 4 grams per day as an intravenous infusion in the form of a sterile physiological salt solution of N-acetyl-L-tyrosine. All test animals after the birth of the first calf showed an acycle. After the infusion the serum tyrosine content increased sharply 1 to 2 days before the ovulation. Insemination after the tyrosine treatment proceeded successfully. Animals which were not inseminated then again showed the regular cycles.

EXAMPLE 2

2,080 grams of a mixture of 1,700 grams of L-tyrosine, 200 grams of stearic acid, 100 grams of sodium stearate and 80 grams of water were agglomerated in a punch press and subsequently dried at 65° C. A tyrosine containing agent produced according to this process in an amount of 40 grams of L-tyrosine was given one time in the frame of a field study of 19 cows in which an acycle lasting 50 days post partum was diagnosed. Three, respectively four, days after the application of tyrosine all of the animals were checked by rectal investigation of the functional condition of the ovaries. In 17 cases there was diagnosed a clear coition ready follicle. In 18 animals rut symptoms were clearly recognizable. In 17 inseminated animals in 11 cases there were cows with pregnancy. Four further animals were inseminated 21 days later. Two of these animals conceived (in all 80% conception).

EXAMPLE 3

The following agent is also suited for application according to Example 2: 2000 grams of a mixture of 1,200 grams of L-tyrosine, 400 grams of a hardened animal fat and 400 grams of calcium stearate were granulated with addition of a 5% gelatin solution at 40°-50° C. In a given case, the granulate can also be filled into gelatin capsules and applied by means of a pill dispenser.

EXAMPLE 4

In a pig producing operation there were dispensed with the fodder in a one-time operation in each case 15 grams of L-tyrosine, to sows 5 days after the dropping of piglets, whereby an L-tyrosine containing agent produced by pressing, in a given case with adjuvants including a mold lubricant, was mixed into a mixture of 47% wheat coarse bran, 3% molasses and 50% L-tyrosine was mixed with the feed for the sow. Ten sows served as a control group. In the same manner the procedure was carried out with the first time sows, in which case two animals served as the control group. The results are tabulated in the table.

TABLE

|  |  | Average Number of Piglets |
|---|---|---|
| Old Sows |  |  |
| Test Group | n = 16 | 11.8 |
| Control Group | n = 10 | 8.6 |
| First Time Sows |  |  |
| Test group | n = 3 | 11.3 |
| Control group | n = 2 | 7.0 |

EXAMPLE 5

Twenty-one bitches of various breeds on the 5th, 6th, and 7th day of the prooestrus received L-tyrosine in an amount in each case of 100 mg per kg bodyweight. Bitches which for 1 to 2 years had not conceived again became pregnant after receiving the tyrosine. The symptoms of heat were intensified after the application and the animals were better covered than in previous heats.

The entire disclosure of German priority application No. P3527356.9 is hereby incorporated by reference.

What is claimed is:

1. A process of increasing fertility in a female mammal having a cycle comprising supplying the female mammal with a sufficient amount of L-tyrosine or an alkali metal or alkaline earth metal salt of L-tyrosine, an alkyl ester of L-tyrosine having 1 to 5 carbon atoms in the alkyl group, glycyl-L-tyrosine, an N-fatty acid acyl substituted L-tyrosine having 2 to 22 carbon atoms in the acyl group or N-hydroxmethyl L-tyrosine to increase the fertility of the mammal.
2. A process according to claim 1 wherein the mammal is a domestic animal.
3. A process according to claim 2 wherein the mammal is a cow, horse, sheep, sow, dog or cat.
4. A process according to claim 3 wherein there is employed L-tyrosine.
5. A process according to claim 3 wherein there is employed glycyl-L-tyrosine.
6. A process according to claim 3 wherein there is employed an N-fatty acid acyl tyrosine.
7. A process according to claim 3 wherein there is employed N-acetyl-L-tyrosine.
8. A process according to claim 1 wherein there is employed the methyl or ethyl ester of tyrosine.
9. A process according to claim 1 wherein there is employed an N-fatty acid acyl tyrosine having 14–22 carbon atoms in the acyl group.
10. A process according to claim 1 wherein there is employed 30 to 200 mg of tyrosine or the equivalent amount of the substituted tyrosine per kg bodyweight of the mammal per day.
11. A process according to claim 10 wherein there is employed 30 to 120 mg of tyrosine or the equivalent amount of the substituted tyrosine per kg bodyweight of the mammal per day.
12. A process according to claim 1 wherein the dosage unit is a granulate containing 1–200 mg of tyrosine or the equivalent amount of the substituted tyrosine.
13. A process according to claim 1 wherein the dosage unit is a pill, pellet or tablet containing 10–500 mg of tyrosine or the equivalent amount of substituted tyrosine.
14. A process according to claim 1 wherein the dosage unit is a briquette containing 200–10,000 mg of tyrosine or the equivalent amount of substituted tyrosine.
15. A process according to claim 1 wherein the tyrosine is supplied with a feedstuff adjuvant.
16. A process according to claim 1 wherein the tyrosine or substituted tyrosine is given in an amount sufficient to stimulate heat or normalize heat in the mammal.
17. A process according to claim 1 wherein the L-tyrosine or substituted L-tyrosine is supplied orally.
18. A process according to claim 1 wherein the L-tyrosine or substituted L-tyrosine is supplied intravenously.

* * * * *